(12) United States Patent
Morris et al.

(10) Patent No.: US 8,323,700 B2
(45) Date of Patent: Dec. 4, 2012

(54) METHOD OF MAKING BONE PARTICLES

(75) Inventors: John W. Morris, Beachwood, NJ (US); Kenneth C. Petersen, Brick, NJ (US); Lawrence A. Shimp, Morganville, NJ (US); Mark P. Daugherty, Allenwood, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 591 days.

(21) Appl. No.: 10/509,585

(22) PCT Filed: Mar. 31, 2003

(86) PCT No.: PCT/US03/09878
§ 371 (c)(1),
(2), (4) Date: Jul. 25, 2005

(87) PCT Pub. No.: WO03/082159
PCT Pub. Date: Oct. 9, 2003

(65) Prior Publication Data
US 2006/0024656 A1    Feb. 2, 2006

Related U.S. Application Data

(60) Provisional application No. 60/368,645, filed on Mar. 29, 2002.

(51) Int. Cl.
*A61K 35/32* (2006.01)
*A61F 2/28* (2006.01)

(52) U.S. Cl. ..................... 424/549; 623/16.11

(58) Field of Classification Search .................. 424/549, 424/548; 623/11.16, 11.18; 435/1.1, 366
See application file for complete search history.

(56) References Cited

U.S. PATENT DOCUMENTS

| | | | |
|---|---|---|---|
| 5,073,373 A | | 12/1991 | O'Leary |
| 5,162,114 A | * | 11/1992 | Kuberasampath et al. ... 424/423 |
| 5,507,813 A | * | 4/1996 | Dowd et al. ................. 623/23.63 |
| 5,899,939 A | * | 5/1999 | Boyce et al. ................. 623/16.11 |
| 5,910,315 A | * | 6/1999 | Stevenson et al. ............ 424/422 |
| 6,311,690 B1 | * | 11/2001 | Jefferies ........................ 128/898 |
| 6,454,811 B1 | * | 9/2002 | Sherwood et al. ......... 623/23.76 |
| 6,863,694 B1 | * | 3/2005 | Boyce et al. ................. 623/23.63 |

FOREIGN PATENT DOCUMENTS

| WO | WO 95/15776 A | 6/1995 |
|---|---|---|
| WO | 01/45760 | 6/2001 |
| WO | WO 02/02156 A2 | 1/2002 |

OTHER PUBLICATIONS

Aaron et al J Histochem Cytochem. Mar. 1987;35(3):361-9.*

* cited by examiner

*Primary Examiner* — Anoop Singh
(74) *Attorney, Agent, or Firm* — Sorell, Lenna & Schmidt, LLP

(57) ABSTRACT

The present invention relates to a method for making bone particles from bone of a variety of sizes and a workpiece forming and holding device for use with the method. The workpiece forming device includes a base and a base frame attached to the surface of the base. An apparatus for forming a solidified mass of bone and immobilization medium is also provided which includes the workpiece forming device and a detachable former member enclosing the base frame. Bone is immersed in an immobilization medium within such workpiece forming device, which is solidified to form a solidified mass of bone and immobilization medium and then subdivided to provide particles of bone in association to with immobilization medium. The immobilization medium may be optionally removed to leave bone particles suitable for use in orthopedic applications including implants.

5 Claims, 2 Drawing Sheets

METHOD OF MAKING BONE PARTICLES

CROSS-REFERENCE TO RELATED APPLICATIONS

This application claims the benefit under 35 U.S.C. §119 (e) of earlier filed and copending U.S. Provisional Application No. 60/368,645, filed Mar. 29, 2002, the contents of which are incorporated by reference herein.

BACKGROUND OF THE INVENTION

1. Field of the Invention

This invention relates to a method for making bone particles useful in a variety of orthopedic applications and to a workpiece forming and holding device for use with the method.

2. Description of Related Art

The manufacture of bone particles, implants containing such particles, and the use of the particles and implants in the repair of bone defects and for other orthopedic applications are known.

The microstructure of cortical bone consists of bundles, or fibers, of mineralized collagen that are oriented parallel to the long axis of the bone. Known methods for making bone particles involve subdividing sections of whole, i.e., mineralized, bone, e.g., by such mechanical operations as shredding, milling, shaving, machining, etc. If desired, the particles can be partially or substantially completely demineralized, e.g., by treatment with acid. The resulting demineralized bone particles exhibit osteoinductive properties that make them useful as, or in, implants intended for use in bone repair and other orthopedic applications.

Because of the mechanical limitations of known and conventional bone milling machinery, e.g., the need to grip the bone stock in the jaws of the machine, only donor bone of fairly substantial size, e.g., intact cortical shafts, can be used as a source for the bone particles. The amount of bone particles that can be produced is limited to some extent by the need to use such relatively large sections of bone. This is a considerable drawback due to the limited availability of donor bone. At this time, regulations do not permit the pooling of donor bone material. Since the quantity of bone particles that can be obtained is limited both by the availability of donor bone and the size of the bone, there is a need for a method of making bone particles that is not subject to the constraints imposed by these limiting factors.

SUMMARY OF THE INVENTION

It is an object of the invention to provide a method of making bone particles from bone, e.g., donor bone.

It is a particular object of the invention to provide a method of making bone particles that results in a greater yield of particles for the available bone compared with that provided by prior art methods.

It is yet another object of the invention to provide demineralized bone particles in the form of fibers or fibrous bundles of bone collagen.

It is still another object of the invention to provide a workpiece holder and workpiece preparation method for use in forming a solidified mass of bone and an immobilization medium for subsequent subdivision into bone particles.

In keeping with these and related objects of the invention, there is provided a method of making bone particles which comprises:

a) immersing a quantity of bone in an immobilization medium;
b) solidifying the immobilization medium to provide a solidified mass of bone and immobilization medium; and,
c) subdividing the solidified mass of bone and immobilization medium to provide subdivided particles of bone In one embodiment, the subdivided particle of bone may be in association with immobilization medium. In such a case, the subdivided particles of bone may optionally be separated from the immobilization medium.

The volume ratio of bone to immobilization medium is preferably from about 1:100 to about 10:1. The immobilization medium is sufficiently rigid, or made to be sufficiently rigid as to anchor itself and the bone contained therein against the forces applied during the subdivision process, which preferably is a milling operation.

The combination of bone and immobilization medium can then be subjected to the subdivision process, which subdivides the embedded bone along with the immobilization medium.

Optionally, the bone particles obtained from the methods of the present invention may then be separated from the immobilization medium. The size of the starting bone material may range from about 200 microns$^3$ to about 15 cm$^3$ in size. Additionally, starting material may comprise a whole bone, or any fragments thereof. The bone particles thus obtained are smaller than the bone utilized as the starting material, with sizes of bone particles preferably ranging from about 150 microns$^3$ to about 14 cm$^3$ in size.

Compositions are also provided comprising one or more bone fragments in combination with an immobilization medium.

A principal advantage of the foregoing method lies in its ability to utilize the relatively small and irregularly shaped bone fragments that result from the processing and/or shaping of a relatively large section or piece of donor bone. More than one piece of donor bone may be utilized. This, in turn, allows for optimum use of donor bone.

Further, in accordance with the invention, there is provided a workpiece forming assembly for forming a solidified mass of bone and immobilization medium which includes a workpiece holder subassembly for securing the solidified mass of bone and immobilization medium in place while the subdivision of the workpiece into particles is being carried out.

The workpiece holder subassembly comprises:
a) a base;
b) a base frame attached to the surface of the base.

An apparatus for forming a solidified mass of bone and immobilization medium is also provided which comprises the foregoing workpiece holder subassembly and a detachable former member enclosing the base frame.

The foregoing devices facilitate the preparation of a solidified mass of bone and immobilization medium which can then be readily subdivided, e.g., by milling or machining, into particles yielding the bone particles of this invention.

The term "particles" as utilized herein is intended to include relatively small bone pieces such as fibers, bundles of loosely connected fibers, threads, narrow strips, thin sheets, chips, shards, powders, etc., that possess regular, irregular or random geometries and which may, or may not be, completely separated from each other.

The expression "whole bone" as utilized herein refers to bone that contains its full naturally occurring mineral content and includes anatomically complete bones and sections thereof.

The term "demineralized" as used herein refers to bone containing less than its entire original mineral context. Thus, the demineralized bone can be partially or substantially fully demineralized and in the case of partially demineralized bone, the demineralization can be uniformly throughout the bone, segmentally present therein or confined to the surface of the bone ("superficially demineralized bone").

The terms "osteogenic" as used herein shall be understood to refer to the ability of a material or substance to induce new bone formation via the participation of living cells from within the substance and "osteogenesis" as the mechanism or result The terms "osteoinductive" as used herein shall be understood to refer to the ability of a material or substance to recruit cells from the host which have osteogenic potential and the ability to form ectopic bone and "osteoinduction" as the mechanism or result.

The terms "osteoconductive" as used herein shall be understood to refer to the ability of a material or substance to provide surfaces that are receptive to the growth of new host bone and "osteoconduction" as the mechanism or result.

The terms "autogenic", "allogenic" and "xenogenic" are used herein relative to the ultimate recipient of the bone tissue.

The term "immobilization medium" as used herein is any material which may be solidified and into which bone may be immersed. Where the immobilization medium is an "immobilization liquid", it preferably is flowable, or can be made flowable (i.e. by melting) under production conditions, and includes readily pourable liquids such as water as well as more viscous substances such as glycerol. Immobilization liquids can be frozen or otherwise converted to a solidified state. The immobilization medium may also be polymers; gases such as carbon dioxide; and other compositions which sublimate, i.e., pass from a solid to gaseous state, and vice-versa, without entering a liquid phase. As used herein, "immobilization medium" includes combinations of more than one media which may be solidified and into which bone may be immersed.

DETAILED DESCRIPTION OF THE INVENTION

Figure 1:
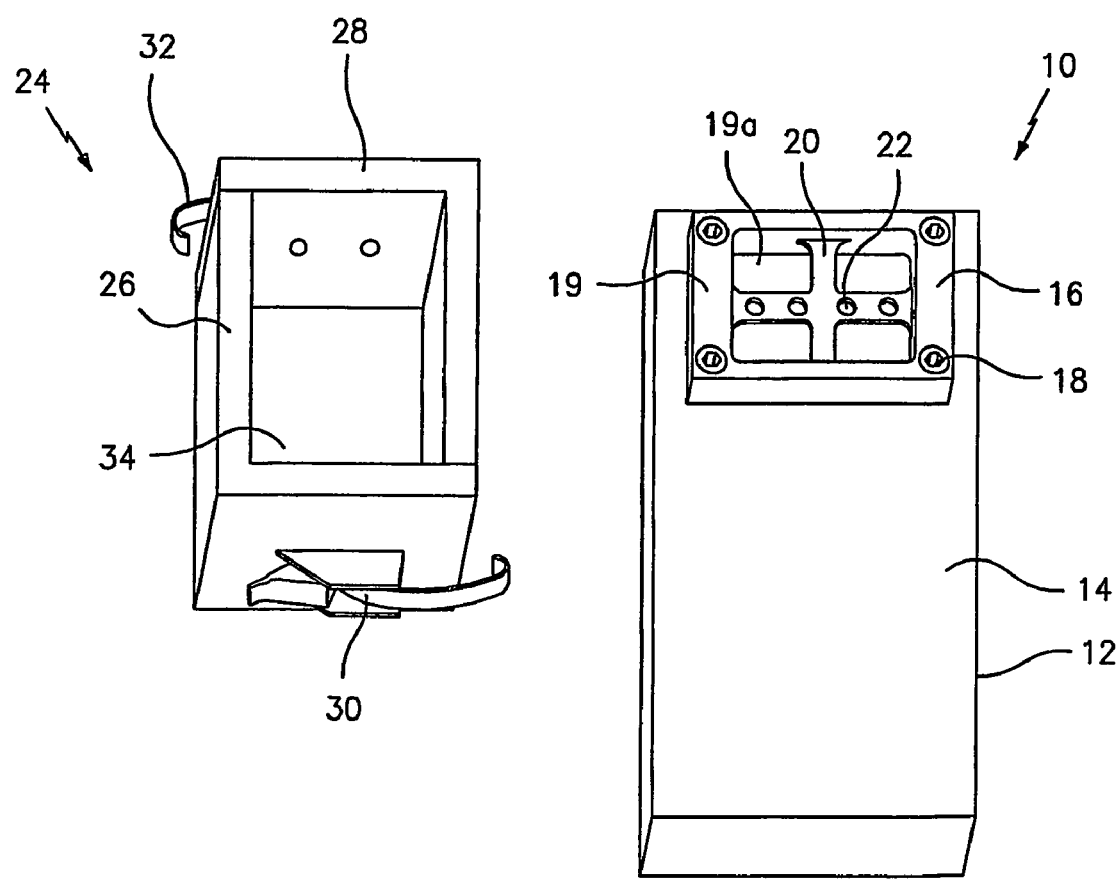
FIG. 1 shows the disassembled components of an apparatus for forming a solidified block-shaped mass of bone and immobilization medium in accordance with the invention.

The bone suitable for making the bone particles of this invention can be from any source. Thus, autogenic, allogenic or xenogenic bone can be used. Especially useful sources of xenogenic tissue may be porcine, equine, or bovine. Preferably, autogenic and allogenic bone are utilized. The bone may be cortical, cancellous or corticocancellous. The most preferred bone is cortical allogenic bone, e.g., femur, tibia, fibula, radius, ulna, etc.

The method of this invention is applicable to bone in a variety of sizes. Therefore, the bone utilized as the starting, or stock, material will range in size from relatively small pieces of bone to bone of such dimensions as to be recognizable as to its anatomical origin. The size of the starting bone material may range from about 200 microns$^3$ to about 15 cm$^3$ in size. In one preferred embodiment, the pieces or sections of whole bone stock can range from about 1 to about 400 mm, and preferably from about 5 to about 100 mm, in median length; from about 0.5 to about 20 mm, and preferably from about 2 to about 10 mm, in median thickness; and from about 1 to about 20 mm, and preferably from about 2 to about 10 mm, in median width. More than one piece of bone may be utilized as the starting or stock material.

After the bone is obtained from the donor, it is processed, e.g., cleaned, disinfected, defatted, etc., using methods well known in the art. If desired, the bone can be either partially or substantially demineralized. Demineralization of the bone can be accomplished in accordance with known and conventional procedures. Demineralization procedures remove the inorganic mineral component of bone by employing acid solutions. Such procedures are well known in the art, see for example, Reddi et al., *Proceeding of the National Academy of Sciences of the United States of America* 69, pp.1601-1605 (1972), incorporated herein by reference. The strength of the acid solution, the shape and size of the bone and the duration of the demineralization procedure will determine the extent of demineralization. Generally speaking, larger bone portions as compared to small particles will require more lengthy and vigorous demineralization. Guidance for specific parameters for the demineralization of different size bone can be found in U.S. Pat. No. 5,846,484, Harakas, Clinical Orthopaedics and Related Research, pp. 239-251(1983) and Lewandrowski et al., *Journal of Biomedical Materials Research*, 31, pp. 365-372 (1996), each of which is incorporated by reference herein.

In a demineralization procedure useful in the practice of the invention herein, the bone is subjected to an optional defatting/disinfecting step that is followed by an acid demineralization step. A useful defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. Ordinarily, at least about 10 to about 40 weight percent by weight of water (i.e., about 60 to about 90 weight percent of a defatting agent such as alcohol) should be present in the defatting/disinfecting solution to produce optimal lipid removal and disinfection within the shortest period of time. A useful concentration range of the defatting solution is from about 60 to about 85 weight percent alcohol, preferably about 65 to about 75 weight percent alcohol, with about 70 weight percent alcohol being most preferred. An alternative or supplemental defatting solution may be made from a surfactant such as Triton X-100 at a concentration of about 0.1% to about 10% in water.

Following defatting, the bone is immersed in acid over time to effect demineralization. Acids which may be employed in this step include inorganic acids such as hydrochloric acid and organic acids such as peracetic acid. After acid treatment, the demineralized bone is rinsed with sterile water to remove residual amounts of acid and thereby raise the pH. Optionally, the defatting step may be carried out simultaneously with the demineralization step.

The bone, fully mineralized or demineralized as described above, is immersed in an immobilization medium. The immobilization medium is then solidified to form a solidified mass comprising the embedded bone. The solidified mass of bone and immobilization medium may then be processed to obtain bone particles of a desired configuration and size. As noted above, more than one piece of bone may be utilized as the starting or stock material, and the bone particles subsequently obtained are smaller than the bone, including any bone fragments or pieces, utilized as the starting or stock material.

In accordance with the present invention, the immobilization medium, once solidified, is subdivided along with the bone contained therein, without the need for any external anchor or support mechanism. In other words, the immobilization medium by itself, once solidified, is able to withstand the forces applied to subdivide the bone contained within the solidified mass of bone and immobilization medium, such that the un-melted portion of the solidified mass of bone and immobilization medium remains intact following each successive subdivision step (e.g., each pass of the mill) to be suitable for the next subdivision step. Preferably, the immobilization medium will be sufficiently rigid to anchor itself and the bone contained therein against the forces applied during milling operations. As a result, the immobilization medium acts as a millable anchor since both the bone and the immobilization medium are subdivided during the subdivision process, providing particles of bone in association with immobilization medium.

In one embodiment, the bone particles may subsequently be separated from the immobilization medium and the bone particles may then be used in an orthopedic application such as an implant.

Suitable immobilization media include liquids, which can be frozen or otherwise converted to a solidified state; polymers; gases such as carbon dioxide (i.e. dry ice); and other compositions which sublimate, i.e., pass from a solid phase to a gas phase and vice-versa without any liquid phase, such as carbon dioxide and naphthalene.

Specific examples of suitable immobilization media include, but are not limited to, water based solutions or suspensions including acids, bases, salts, and polymers; organic liquids and solutions including solutions of polymers; materials that are liquid below about 80° C. and can be solidified by cooling; materials that solidify through chemical action; materials that solidify upon removal of a solvent; and materials that crystallize to form solids.

Other examples of suitable immobilization media include, but are not limited to water; glycerol; propylene glycol; polyethylene glycol; alcohols, e.g., ethanol; detergents, e.g. sodium dodecylsulfate; surfactants, e.g., octylphenol polyethoxylate (commercially available as Triton X-100), Igepal CA-630 (which is chemically similar to, but slightly less hydrophilic than, Triton X-100), nonionic surfactants such as alcohol ethoxylates, which are more biodegradable and have less adverse health effects, Neodols, Tergitols and others; demineralization solutions, e.g., acids such as hydrochloric acid and peracetic acid. These media may be subjected to treatment after the process of subdividing the solidified mass into particles to remove the immobilization medium, leaving the bone particles. For example, particles in combination with an immobilization medium which is solidified by freezing may be allowed to melt, leaving just the bone particles. Similarly, an immobilization medium which is solid at room temperature, such as a polyethylene glycol, may be heated after the process of subdividing the solidified mass into particles, leaving just the bone particles.

Suitable polymers which may be used as an immobilization medium should be either polymerizable or thermosettable and include, but are not limited to, polystyrene and polyvinyl chloride. Where a polymerizable material is used, the immobilization medium may optimally be removed with a solvent such as acetone, methylene chloride, cyclohexanone, liquid hydrocarbons, etc., leaving the bone particles.

Materials that solidify upon solvent removal may also be used as an immobilization media. Examples include sugar and water, or an acetone solution of polystyrene.

Materials that crystallize to form a solid may also be used as an immobilization medium. An example is sodium tripolyphosphate precipitated from an aqueous solution.

Suitable materials which sublimate and may be used as an immobilization medium include, but are not limited to, carbon dioxide (dry ice); and naphthalene. Such an immobilization medium may be solidified by freezing and, subsequent to the process of subdividing it into particles, the immobilization medium may optionally be removed by allowing the solid form to melt or by heating, leaving the bone particles behind.

Where the immobilization medium is preferably flowable, or made flowable (i.e. by melting) it can readily be solidified under appropriate production conditions to create a solidified mass of bone and immobilization medium.

Preferably, the immobilization medium is kept below its triple point (the temperature and pressure at which its gas, liquid and solid phases co-exist in equilibrium) so the solidified mass won't fall apart during the process of subdividing it into particles.

The present invention is also directed to a workpiece holder and an apparatus for forming a solidified mass of bone and immobilization medium for subsequent subdivision into particles. The workpiece holder includes a base and a base frame attached to the surface of the base. The apparatus comprises the workpiece holder and includes a detachable former member enclosing the base frame. The base frame of the apparatus or workpiece holder holds the solid mass of bone and immobilization medium, which may then be subdivided to provide particles. Bone is at least partially immersed in an immobilization medium within such workpiece holder and then solidified to form a mass of bone and immobilization medium. The immobilization medium acts as a millable anchor by forming a solidified mass, the entirety of which may be milled without any external support.

In one embodiment, the base of the workpiece holder possesses a passageway for the circulation of a refrigerant therethrough. Where the immobilization medium would normally be in the gas or liquid phase at room temperature, it may be necessary to cool the solidified mass of bone and immobilization medium, also referred to as the workpiece, and the apparatus holding the solidified mass to maintain the temperature below the triple point of the immobilization medium. In such a case, a refrigerant may be circulated through the base of the workpiece holder used in forming the solidified mass of bone and immobilization medium. Suitable refrigerants are known to those skilled in the art and include, but are not limited to, water, aqueous solutions, water/organic mixtures, such as water/alcohol mixtures, organic liquids, fluorocarbon or chloro-fluorocarbon refrigerants, ammonia, propylene glycol or ethylene glycovwater solutions, brine solutions, alcohol solutions, liquefied gasses such as liquid nitrogen, and cooled gasses.

In another embodiment, the base of the workpiece holder may possess a thermoelectric device to regulate the temperature of the workpiece and workpiece holder. Such thermoelectric devices include thermal electric systems and thermoconductive materials known to those skilled in the art. Suitable thermoconductive materials, also known as Peltier materials, include semiconductors such as bismuth telluride, antimony telluride, sandwiched between ceramic plates made of aluminum oxide, aluminum nitride, beryllium oxide, etc.

Electrical conductors such as copper films or silver films may be applied to the internal surface of the ceramic plates which may be soldered or glued together.

Phase change materials such as crystals of calcium chloride may also be used as a refrigerant.

Solid refrigerants, such as dry ice, may be used by packing them around the frozen mass of immobilization medium and bone, or by packing the solid refrigerant around the support for the bone/immobilization medium and having the support conduct the cold to the bone/immobilization medium. Such refrigerants may be contained in a container around the workpiece or its base.

Similarly, phase-change materials such as calcium chloride or a cooled liquid refrigerant, such as a brine solution, may be encased in a container around the workpiece or its base.

Once the solidified mass of bone and immobilization medium is formed, the solidified mass undergoes a subdivision process to provide particles of bone in association with immobilization medium. Preferably, the volume ratio of bone to immobilization medium in these particles ranges from about 1:100 to about 10:1. As noted above, while not required, in some embodiments it may be preferable to remove the immobilization medium from the bone particles subsequent to the subdivision process. Useful equipment for the subdivision of the solidified mass of bone and immobilization medium are machines known in the art, e.g., shredding, milling, pressing, shaving, machining, extruding and/or cutting machines. Many of the preferred machines for the subdivision of the demineralized bone will fragment the demineralized bone, by cutting or separating the demineralized material in direction parallel or nearly parallel to the underlying collagen fibers. Mills, presses and extruders are particularly useful in this regards. Particularly preferred machines are mills, including impact mills, grating mills, shearing mills and cutting mills. Most preferred are mills that utilize a machining process, such as those disclosed in U.S. Pat. No. 5,607,269, the contents of which are incorporated by reference herein.

An impact mill has blunt rotors or swinging hammers that move at high speed and subdivide the demineralized bone stock by impacting upon the bone shattering it into fragmentary particles. The bone tends to shatter along the lines of the natural collagen bundles constituting the microstructure of the bone. Similar mills with sharp cutting rotors tend to chop the bone into somewhat symmetric particles as opposed to the fibrous particles obtained with an impact mill. Impact speed is a factor that influences the result. Too low a speed may cause the bone to plastically deform rather than shatter into particles as required. This and similar factors involved in the operation of a particular type or model of impact mill to provide demineralized bone fibers can be optimized employing routine experimentation.

A shearing mill subdivides bone by tearing the bone apart. The tearing action tends to preferentially break the bone apart at its weakest point. In the case of demineralized bone, the junctions between demineralized collagen bundles represent weak points and the result is the production of fiber type particles.

The spindle element of a lathe can be adapted to carry a rotary grinding wheel whose circumferential surface is studded with projecting cutting elements. As the bone stock is pressed against the rotating wheel, the cutting elements produce fiber-type particles. In this type of particle-forming operation, the resulting fibrous particles are not separated along the lines of natural collagen bundles.

In one embodiment, the bone may not be fully embedded in the immobilization medium, but rather be partially embedded so that the immobilization medium serves as an attachment point or points for connection to a lathe or other similar machine, thus enabling only the bone to be subdivided leaving the immobilization medium intact.

In another embodiment, the bone may not be fully embedded in the immobilization medium, but rather be partially embedded so that the immobilization medium serves as an anchor point or points and portions of the bone protrude from the immobilization medium so that they may be to be subdivided by a mill.

Still other apparatus useful in milling bone particles according to the invention include mills available from IKA® Works (Wilmington, N.C.) such as the model A 10 IKA-Analytical Mill or the model M 20 IKA-Universal Mill. Such mills have cooling connections and are suitable for the grinding of hard and brittle substances with a maximum grain size of 6-7 mm. It has been determined that a stainless steel star-shaped cutter provides particles of a useful size. Other milling machines useful in the practice of the invention herein include drum cutter bone mills such as those available from Tracer Designs, Inc. (Santa Paula, Calif.), e.g., its bone mill model BM1000.

In some cases it may be preferable to not only circulate a refrigerant through the base of the workpiece holder, but to subject the workpiece, the milling device, the base frame of the workpiece holder, and any other component utilized in the present invention to a cooling process. Such cooling processes are known to those skilled in the art and can include the use of a cooling connection on a mill in conjunction with refrigeration or, as described above, the use of a refrigerant circulated within the workpiece holder or encasing solid or liquid refrigerants in a container around the workpiece holder or its base.

Bone particles produced in accordance with the methods of the present invention may range from about 150 microns$^3$ to about 14 cm$^3$ in size.

As noted above, in one embodiment the immobilization medium is separated from the bone particles after the subdivision process leaving just the bone particles, which may then be used in an orthopedic application such as an implant.

Depending on the procedure employed for producing the bone particles, one can obtain a mass of bone particles in which at least about 80 weight percent, preferably at least about 90 weight percent, and most preferably at least about 95 weight percent, of the particles possess a median length of from about 2 to about 300 mm or greater, preferably a median length of from about 5 to about 50 mm; a median thickness of from about 0.5 to about 15 mm, preferably a median thickness of from about 1 to about 5 mm; a median width of from about 2 to about 35 mm, preferably a median width of from about 2 to about 20 mm; and a median length to thickness ratio and/or a median length to width ratio of from about 2:1 to about 200:1, preferably from about 10:1 to about 100:1. Elongate bone particles of this kind are described in U.S. Pat. Nos. 5,507,813 and 5,314,476, the contents of each of which are incorporated by reference herein.

In another embodiment, it may be desirable to obtain particles which are mainly fibrous in nature. Preferably, the fibers obtained by the methods of the present invention have varied orientations relative to the collagen fibrils of the donor bone, especially where a single piece of bone is used as donor bone. These fibers, with different orientations, have many junctions where fragments of fibers cross. These junctions increase the fiber roughness which helps in creating a coherent mass, especially when the fibers have been demineralized. A coherent mass may be especially useful in creating bone grafting materials that stay in place and resist dislodgement by blood flow or irrigation.

If desired, the mass of bone particles can be graded or sorted into different sizes, e.g., by screening, and/or any less desirable size(s) of bone particles that may be present can be reduced or eliminated.

At this time, depending upon their intended final usage, the bone particles may be utilized as is or stored under aseptic conditions, advantageously in a lyophilized or frozen state, for use at a later time.

The mineralized and demineralized bone particles of this invention find use as, or in, implants for a variety of orthopedic procedures where they participate in the bone healing/repair process through one or more mechanisms such as osteogenesis, osteoinduction and osteoconduction. The bone particles can be used as is, or formed into a variety of product types such as gels, putties, or sheets. The demineralized bone particles can optionally be admixed with one or more substances such as adhesives, fillers, plasticizers, flexibilizing agents, biostatic/biocidal agents, medically/surgically useful substances, surface active agents, binding and bonding agents, and the like, prior to, during, or after shaping the particles into a desired configuration.

The method and apparatus of the invention will now be described in connection with FIGS. 1, 2 and 3. While many different immobilization media may be utilized in accordance with the present invention, the following description utilizes a liquid as the immobilization medium. However, the apparatus and methods of FIGS. 1-3 may just as easily be used with a polymer, a gas, or a material which undergoes sublimation.

Referring to FIG. 1, an apparatus for forming a solidified mass of bone and immobilization medium is shown in a disassembled condition. Apparatus 10 includes base plate 12 having a generally flat upper surface 14. Base frame 16 is secured to upper surface 14 of base plate 12 by bolts 18. Base frame 16 includes rectangular circumferential portions 19 defining an inner cavity 19a, and anchoring element 20 for bridging inner cavity 19a. This arrangement allows base frame 16 to hold a workpiece of solidified bone and immobilization medium in place during the machining of the workpiece into particles. A plurality of holes 22 are disposed along anchoring element 20 for facilitating anchoring of the solidified mass to the base frame.

Apparatus 10 further includes detachable former member 24 possessing separable wall members 26 and 28 of L-type configuration, respectively, and wall member retaining clips 30 and 32 for locking wall members 26 and 28 together in a liquid-tight manner. Wall members 26 and 28 together define a central enclosure 34 configured and dimensioned to enclose base frame 16. Base plate 12, base frame 16 and former member 24 are preferably made of metal, advantageously, stainless steel. Optionally, base plate 12 can be provided with passageways for the internal circulation of refrigerant This will permit the base plate to remain at an appropriately reduced temperature, maintaining the mass of bone and immobilization medium once formed in the solidified state during the milling operation described below in connection with FIGS. 2 and 3. Where the immobilization medium is a liquid, the refrigerant helps maintain the bone and immobilization liquid in a frozen state.

Referring still to FIG. 1, the method of forming a solidified mass of bone and an immobilization medium to serve as a workpiece for the machining operation which follows utilizes above-described apparatus 10. For purposes of the following description, water is utilized as the immobilization medium but, as noted above, numerous other immobilization media, including combinations thereof, may be used with the workpiece holder and apparatus described herein to form a solidified mass of bone and immobilization medium.

In utilizing apparatus 10, wall members 26 and 28 of former member 24 are first placed on base 12 to enclose base frame 16 and retaining clips 30 and 32 on the wall members are locked in place. The assembly is then placed in a freezer for a suitable time, e.g., about 10 minutes, at a low temperature, e.g., about −70° F. Clean process water (e.g., distilled water) is then poured into central enclosure 34 of former member 24 to about ⅛ inch above the upper surface of base frame 16. The apparatus is again subjected to a reduced temperature environment for a suitable time, e.g., about 10 minutes, until the water is frozen.

A quantity of bone, e.g., in the form of irregularly shaped bone pieces or fragments, is then placed upon the surface of the ice and another quantity of process water is poured on top of the bone until the bone is substantially immersed in the water. The assembly is once again subjected to the reduced temperature environment, e.g., for about 40 minutes, until the process water has frozen, thereby forming the workpiece of frozen bone and immobilization liquid. Retaining clips 30 and 32 are unlocked and wall members 26 and 28 are detached from the workpiece.

Figure 2:
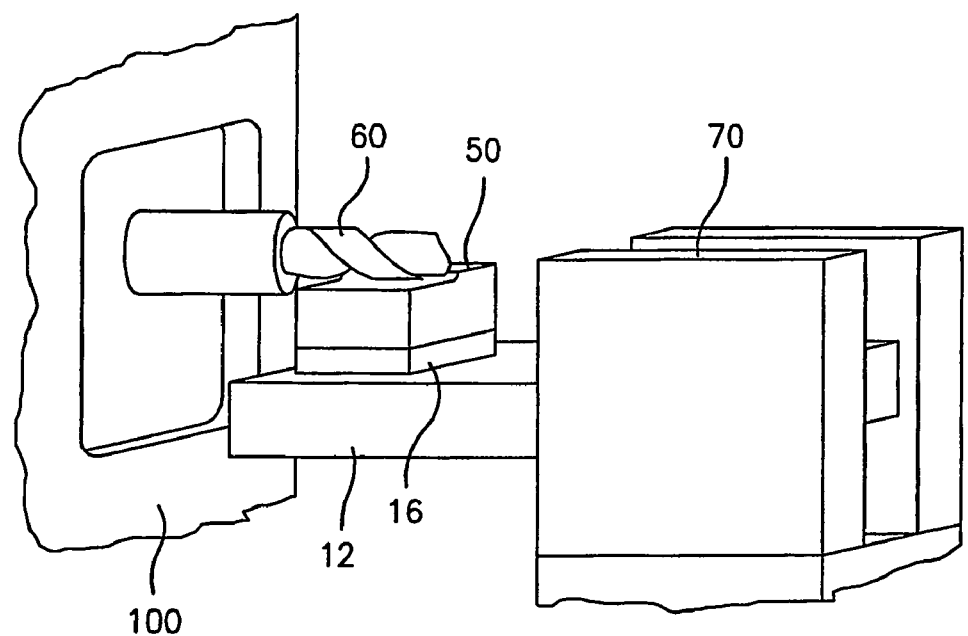
FIG. 2 shows the solidified mass of bone and immobilization medium (workpiece) anchored in place upon the base of the workpiece holder by the base frame with the base being locked within a clamp or vise to secure the workpiece holder from movement during the milling of the workpiece; and, FIG. 3 shows the cutting bit of a milling unit forming elongate particles of bone from the solidified mass of bone and immobilization medium.
Figure 3:
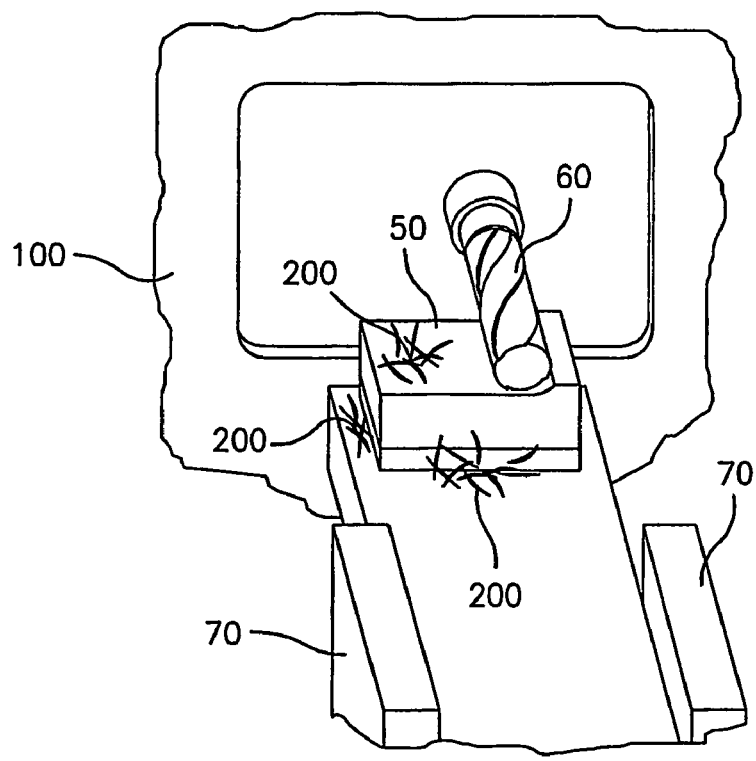

Referring now to FIGS. 2 and 3, the method of making bone particles using the apparatus will now be described.

A workpiece holder, with its mass SO of frozen bone and immobilization liquid anchored firmly in place in base frame 16, is itself secured in a fixed position relative to the cutting bit 60 of milling machine 100 by vise, or clamp, 70 which holds base 12. With the milling machine 100 set to an appropriate operation condition, e.g., RPM and table feed speed, etc., the milling operation is carried out to provide the bone particles. FIGS. 2 and 3 illustrate the operation of making elongate bone particles 200 upon rotation of milling bit 60 while the milling table (or the milling head including bit 60) traverses back and forth. Upon completion of the milling operation, the resultant bone particles in association with ice are collected and the ice is permitted to melt. The bone particles may then be dried and/or further processed as desired.

In another embodiment, the mill comprises a device which is effective to clear the milled fibers from the solidified mass after they have been milled. This device may be a pusher bar or brush attached to the mill so that it tracks along with the milling bit.

The method of this invention will be better understood by way of the following example. This example is provided as a means of explaining the invention herein wherein the bone is immersed in a liquid immobilization medium and is not intended to limit the invention in any way.

EXAMPLE

Assembled workpiece forming apparatus 10 described above, was placed in a freezer at −70° F. for 10 minutes to chill the apparatus. Process water was then introduced into central enclosure 34 to a level of about 1 cm above base frame 16. Because apparatus 10 had already been chilled to a low temperature, the water immediately froze at the gaps between former member 24 and base plate 12 thus preventing leaks. After 10 more minutes in the freezer, the water was completely frozen and bone fragments could be added. The bone consisted of human femoral, tibial, and humerus shaft sections (about 10 mm to 40 mm long). For optimum packing density, the shaft sections were split along their axial dimension to form planks. The planks were placed upon the surface of the ice within central enclosure 34 with the axes of the bone fragments (relative to their medullary canals) aligned with the axis of base plate 12. The total amount of bone was about 150 grams. Process water was then poured into central enclosure 34 until all of the bone pieces were fully immersed. After 40 more minutes in the freezer, the bone was completely frozen in ice. At this point, apparatus 10 was removed from the freezer, former member 24 was disassembled and removed, and the resulting subassembly, consisting of the frozen block of bone fragments anchored to base plate 12, was held in a vise in a predetermined fixed position relative to milling bit 60 of milling machine 100 as shown in FIGS. 2 and 3 so that the bone could be milled into fibers. One exemplary milling machine and operating procedure is described in U.S. Pat. No. 5,607,269, the contents of which are incorporated by reference herein.

Milling the frozen bone block took about 1 hour. No additional cooling was needed; the block remained frozen throughout the milling process. Because the bone had been placed upon a layer of ice above base frame 16 of base plate 12, there was no risk of the milling bit cutting down into the frame. The yield of bone fibers was about 145 grams (97%). All of the recovered fibers had a minimum length of 10 mm, with the longest being about 40 mm. In other words, the fiber lengths corresponded to the lengths of the bone fragments.

Various modifications of the disclosure herein in view of the specification, including using combinations of immobilization media, will be obvious to one skilled in the art. For instance, more than one immobilization media may be utilized and solidified to form a solidified mass of bone and immobilization media, which may then be subdivided. Such modifications are intended to be within the scope of the disclosure herein as defined by the specification including the figures contained herein.

What is claimed is:

1. A method of making bone particles, said method comprises:
   a) immersing one or more demineralized bones and/or a demineralized bone section in an immobilization medium;
   b) effecting a phase change of the immobilization medium to convert the immobilization medium to a solid state, thereby solidifying the immobilization medium to provide a solidified mass of bone and immobilization medium;
   c) subdividing the solidified mass of bone and immobilization medium to provide subdivided particles of bone that are in association with immobilization medium; and
   d) separating bone particles from the immobilization medium to provide bone particles for orthopedic implantation.

2. The method of claim 1 wherein the immobilization medium is sufficiently rigid to anchor itself and the bone contained therein against the forces applied during a milling operation.

3. The method of claim 1 wherein the immobilization medium is selected from the group consisting of water, water based acid solutions, water based basic solutions, water based salt solutions, water based polymer solutions, organic liquids, carbon dioxide, solutions of polymers, materials that are liquid below about 80° C. and can be solidified by cooling, materials that solidify through chemical action, materials that solidify upon removal of a solvent, and materials that crystallize to form solids.

4. The method of claim 1 wherein the immobilization medium is glycerol, propylene glycol, polyethylene glycol, ethanol, hydrochloric acid, peracetic acid, polystyrene, or polyvinyl chloride.

5. The method of claim 1 wherein the immobilization medium is a composition which sublimates.

* * * * *